(12) United States Patent
Bresler et al.

(10) Patent No.: US 8,198,502 B2
(45) Date of Patent: Jun. 12, 2012

(54) PROCESS FOR SEPARATING PARA-XYLENE FROM A MIXTURE OF C8 AND C9 AROMATIC HYDROCARBONS

(75) Inventors: Leonid Bresler, Northbrook, IL (US); Stanley J. Frey, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 282 days.

(21) Appl. No.: 12/719,410

(22) Filed: Mar. 8, 2010

(65) Prior Publication Data

US 2010/0249483 A1 Sep. 30, 2010

Related U.S. Application Data

(60) Provisional application No. 61/165,246, filed on Mar. 31, 2009.

(51) Int. Cl.
*C07C 7/13* (2006.01)

(52) U.S. Cl. ........ 585/805; 585/820; 585/822; 585/825; 585/826; 585/828

(58) Field of Classification Search .................. None
See application file for complete search history.

(56) References Cited

U.S. PATENT DOCUMENTS

| 339,211 A | 7/1968 | Rosset |
|---|---|---|
| 351,042 A | 5/1970 | Neuzil et al. |
| 368,634 A | 8/1972 | Neuzil |
| 369,610 A | 10/1972 | Neuzil |
| 381,345 A | 5/1974 | Bieser |
| 410,159 A | 7/1978 | Howard, Jr. |
| 488,693 A | 12/1989 | Zinnen |
| 501,203 A | 4/1991 | Zinnen |
| 505,764 A | 10/1991 | Zinnen |
| 517,192 A | 12/1992 | Anderson |
| 517,729 A | 1/1993 | Oroskar et al. |
| 6,573,418 B2 | 6/2003 | Miller et al. |
| 6,600,083 B2 | 7/2003 | Doyle et al. |
| 6,627,783 B2 | 9/2003 | Doyle et al. |
| 6,689,929 B2 | 2/2004 | Williams et al. |
| 6,878,855 B2 | 4/2005 | Deckman et al. |
| 2007/0299289 A1 | 12/2007 | Bresler et al. |
| 2009/0324457 A1 | 12/2009 | Bresler et al. |
| 2009/0326306 A1 | 12/2009 | Bresler et al. |

*Primary Examiner* — Tam M Nguyen
(74) *Attorney, Agent, or Firm* — Mark R Willis

(57) ABSTRACT

The invention is an adsorptive separation process for producing a para-xylene product from a feed stream comprising para-xylene, at least one other C8 aromatic, and a C9 aromatic. An adsorbent comprising X or Y zeolite and a desorbent comprising para-diethylbenzene (p-DEB) are used in an adsorptive separation zone to produce an extract stream comprising para-xylene, p-DEB, and the C9 aromatic and a raffinate stream comprising the at least one other C8 aromatic, the C9 aromatic, and p-DEB. The extract stream is separated in an extract distillation zone to produce a second desorbent stream comprising the C9 aromatic and p-DEB and the raffinate stream is separated in a raffinate distillation zone to produce a third desorbent stream comprising the C9 aromatic and p-DEB. At least a portion of at least one of the second desorbent stream and the third desorbent stream is further separated in a desorbent distillation zone to produce a stream comprising the C9 aromatic.

20 Claims, 3 Drawing Sheets

PROCESS FOR SEPARATING PARA-XYLENE FROM A MIXTURE OF C8 AND C9 AROMATIC HYDROCARBONS

CROSS-REFERENCE TO RELATED APPLICATION

This application claims the benefit of U.S. Provisional Application No. 61/165,246 filed Mar. 31, 2009.

FIELD OF THE INVENTION

The present invention pertains to processes for the adsorptive separation of para-xylene from a mixture of C8 and C9 aromatic hydrocarbons wherein the desorbent comprises para-diethylbenzene.

BACKGROUND OF THE INVENTION

Para-xylene is an important raw material in the chemical and fiber industries. For example, terephthalic acid derived from para-xylene is used to produce polyester fabrics. Para-xylene is usually separated from a mixture of para-xylene and at least one other C8 aromatic hydrocarbon by either crystallization, adsorptive separation, or a combination of these two techniques.

U.S. Pat. No. 5,012,038 discloses that para-diethylbenzene (p-DEB) has become a commercial standard as a desorbent for the separation of para-xylene from other xylene isomers, but that p-DEB suffers in the process for separating para-xylene from feed mixtures containing C9 aromatics because the boiling point of p-DEB is too close to the boiling points of C9 aromatics in the feed. This reference also discloses that because C9 aromatics are difficult to separate from p-DEB by simple fractionation, the C9 aromatics would gradually build up in the desorbent which must be recycled for economic reasons; therefore, it has become necessary to reduce C9 aromatics in the feed to below about 0.1% prior to the adsorptive separation of para-xylenes.

R. A. Meyers, Handbook of Petroleum Refining Processes second edition McGraw-Hill Book Company (1997) in Chapter 2.6 discloses an adsorptive separation process for separating para-xylene from other xylene isomers. Feedstock specifications disclosed at page 2.48 of the chapter include maximum limits of 100 ppm for methylethylbenzenes and 500 ppm for other C9 aromatics.

U.S. Pat. No. 5,012,038; U.S. Pat. No. 4,886,930; U.S. Pat. No. 5,057,643; U.S. Pat. No. 5,171,922; U.S. Pat. No. 5,177,295; and U.S. Pat. No. 5,495,061 disclose the use of desorbents having higher boiling points than p-DEB to separate para-xylene from a feed mixture that contains C8 and C9 aromatics. The C9 aromatics are then separated from the higher boiling desorbent by fractionation. However, despite the benefits provided by the higher boiling adsorbents, p-DEB continues to be a commonly used desorbent for the adsorptive separation of para-xylene from C8 aromatic hydrocarbons. Thus, there remains a need in the art for improved processes that enable the separation or recovery of multiple components from C8 and C9 aromatic hydrocarbon mixtures.

SUMMARY OF THE INVENTION

The invention enables adsorptive separation processes for producing a para-xylene product from a feed stream comprising C8 and C9 aromatic hydrocarbons wherein the desorbent comprises para-diethylbenzene (p-DEB) and a C9 aromatic is separated from p-DEB via distillation.

In an embodiment, the invention is a process for separating para-xylene from a feed stream comprising para-xylene, at least one other C8 aromatic, and a C9 aromatic, the process comprising:

(a) contacting an adsorbent comprising a zeolite with the feed stream and a first desorbent stream in an adsorptive separation zone to produce an extract stream and a raffinate stream, the zeolite selected from the group of zeolites consisting of Y zeolites and X zeolites, the first desorbent stream comprising para-diethylbenzene, the extract stream comprising para-xylene, para-diethylbenzene, and the C9 aromatic, and the raffinate stream comprising para-diethylbenzene, the at least one other C8 aromatic, and the C9 aromatic;

(b) passing the extract stream to an extract distillation zone to produce a para-xylene product stream, and a second desorbent stream comprising para-diethylbenzene and the C9 aromatic;

(c) passing the raffinate stream to a raffinate distillation zone to produce a raffinate product stream comprising the at least one other C8 aromatic, and a third desorbent stream comprising para-diethylbenzene and the C9 aromatic;

(d) passing at least a portion of at least one of the second desorbent stream and the third desorbent stream to a desorbent distillation zone to produce a fourth desorbent stream comprising para-diethylbenzene, and a C9 aromatic product stream comprising the C9 aromatic; and (e) recycling at least a portion of the fourth desorbent stream to step (a) as at least a portion of the first desorbent stream.

In an embodiment, the adsorptive separation zone operates in a simulated moving bed mode. In another embodiment, the first desorbent stream may comprise up to 25 wt % of C9 aromatic hydrocarbons. Other embodiments of the present invention encompass further details the descriptions of which, including preferred and optional features are hereinafter disclosed.

The Figures are helpful for an understanding of the present invention and are not intended to limit the scope of the invention as set forth in the claims. Details of the process zones, well known in the art, such as pumps, control valves, instrumentation, heat-recovery circuits, and similar hardware which are non-essential to an understanding of the invention are not illustrated.

DETAILED DESCRIPTION OF THE INVENTION

The feed stream separated by the invention is a mixture comprising at least three components: para-xylene, at least one other C8 aromatic, and a C9 aromatic. Other C8 aromatics include meta-xylene, ortho-xylene, and ethylbenzene. In an embodiment, the C9 aromatic is selected from the group consisting of 135-trimethylbenzene, 123-trimethylbenzene, 124-trimethylbenzene, n-propylbenzene, isopropylbenzene, para-methylethylbenzene, meta-methylethylbenzene, ortho-methylethylbenzene, and combinations thereof. The feed stream may comprise several or all of the C8 and C9 aromatic hydrocarbons and small amounts of other compounds or impurities, for example, when the feed is derived from one or more oil refining processes such as catalytic reforming, stream cracking, crystallizer mother liquors, transalkylation, and xylene isomerization.

The feed stream to be processed by this invention may comprise as much as 25 wt % of the C9 aromatic. In an embodiment, the feed stream comprises from about 0.1 wt % to about 15 wt % of the C9 aromatic; and the feed stream may comprise from about 0.3 wt % to about 5 wt % of the C9 aromatic. In another embodiment, the feed stream may comprise from about 6 wt % to about 15 wt % C9 aromatics. Feed streams having less than about 0.1 wt % C9 aromatics may be processed by this invention. In an embodiment, the feed stream may not contain more than about 10 ppm-mass C10+ aromatic hydrocarbons.

As used herein, the term "stream" can be a stream including various hydrocarbon molecules, such as straight-chain, branched, or cyclic alkanes, alkenes, alkadienes, and alkynes, and optionally other substances or impurities, such as, hydrogen, metals, and sulfur. The stream can also include aromatic and non-aromatic hydrocarbons. Moreover, the hydrocarbon molecules may be abbreviated C1, C2, C3 . . . Cn where "n" represents the number of carbon atoms in the hydrocarbon molecule. As used herein, the term "aromatic" means a hydrocarbon containing one or more rings of unsaturated cyclic carbon radicals where one or more of the carbon radicals can be replaced by one or more non-carbon radicals. An exemplary aromatic compound is benzene having a C6 ring containing three double bonds.

Figure 1:
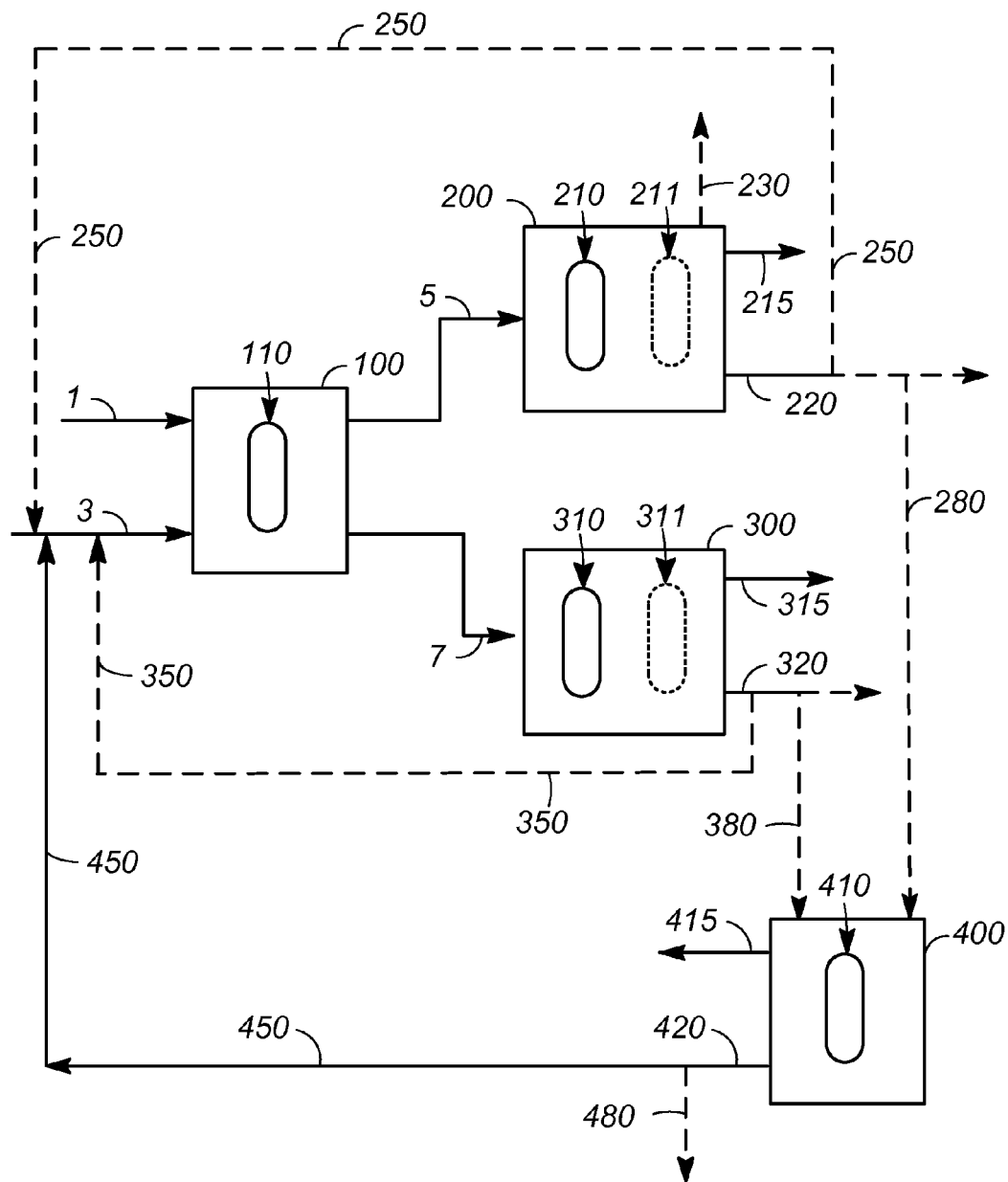
FIG. 1 is a simplified flow scheme illustrating embodiments of the invention.

FIG. 1 is a flow scheme illustrating embodiments of the invention and some of the optional and/or alternate steps encompassed by the invention. The feed stream and a desorbent stream are introduced to adsorptive separation zone 100 via feed conduit 1 and desorbent conduit 3, respectively. Adsorptive separation zone 100 comprises adsorbent chamber 110 containing an adsorbent selective for para-xylene over the other C8 aromatic hydrocarbons in the feed. Adsorptive separation zone 100 produces an extract stream carried by extract conduit 5 and a raffinate stream carried by raffinate conduit 7. In the Figures, reference numbers of the streams and the lines or conduits in which they flow are the same. As used herein, the term "zone" can refer to one or more equipment items and/or one or more sub-zones. Equipment items may include, for example, one or more vessels, heaters, separators, exchangers, conduits, pumps, compressors, and controllers. Additionally, an equipment item can further include one or more zones or sub-zones.

Adsorptive separation processes are well known in the art. In brief summary, a feed stream and desorbent stream are introduced to an adsorbent chamber which may include one or more vessels containing an adsorbent. During an adsorption step, the adsorbent contacts the feed and selectively retains a feed component or a class of feed components relative to the remaining feed components. The selectively retained feed component(s) are released or desorbed from the adsorbent by contacting the adsorbent with the desorbent. Thus, the adsorptive separation process produces an extract stream comprising the selectively adsorbed component or class of components and a raffinate stream comprising the remaining feed components that are less selectively adsorbed. The desorbent stream may comprise one or more desorbent components and use of multiple desorbent streams is also known in the art. The extract and raffinate streams passing from the adsorbent chamber typically also comprise one or more desorbent components.

A variety of adsorptive separation techniques are well known in the art including fixed bed such as operating in a batch or swing bed mode, moving bed, and simulated moving bed (SMB). The invention is not intended to be limited by the particular adsorptive separation technique or mode of operation. Additional information regarding adsorptive separation principles and detail are readily available, e.g., Kirk-Othmer Encyclopedia of Chemical Technology Vol. 1, 3rd ed., Adsorptive Separation (Liquids) pp 563-581, 1978 and Preparative and Production Scale Chromatography edited by G. Ganetsos and P. E. Barker, 1993.

As these various adsorptive separation processes operate on the same basic chromatographic separation principles, the following discussion of adsorbents and desorbents applies to the various adsorptive separation techniques or modes. The functions and properties of adsorbent and desorbents in the chromatographic separation of liquid components are well-known, but for reference thereto, U.S. Pat. No. 4,642,397 is herein incorporated by reference.

Adsorbents which are selective for para-xylene relative to the other C8 aromatic isomers are suitable for use in adsorptive separation zone 100. X and Y zeolites are well known in the art for separating para-xylene from other C8 aromatic hydrocarbons. Optionally, these zeolites may contain IUPAC Group 1 or 2 metal ions at exchangeable cation sites. In an embodiment, the adsorbent comprises X zeolite or Y zeolite. Optionally, the adsorbent may comprise barium, potassium, or both barium and potassium.

It is also known that crystalline aluminosilicates, i.e., zeolites, are used in adsorptive separations of various mixtures in the form of agglomerates having high physical strength and attrition resistance. Methods for forming the crystalline powders into such agglomerates include the addition of an inorganic binder, generally a clay comprising a silicon dioxide and aluminum oxide, to the high purity zeolite powder in wet mixture. The blended clay zeolite mixture is extruded into cylindrical type pellets or formed into beads which are subsequently calcined in order to convert the clay to an amorphous binder of considerable mechanical strength. As binders, clays of the kaolin type, water permeable organic polymers, or silica are generally used.

The desorbent stream in line or conduit 3 introduced to adsorptive separation zone 100 comprises para-diethylbenzene (p-DEB). The desorbent stream may also comprise one or more additional desorbent compounds and/or other components. Desorbent stream 3 may comprise at least trace amounts of C9 aromatics, for example, at least about 20 ppm by weight of C9 aromatics. In an embodiment, desorbent stream 3 introduced to adsorptive separation zone 100 comprises at least about 75 wt % p-DEB. In another embodiment desorbent stream 3 comprises at least about 85 wt % p-DEB; desorbent stream 3 may comprise at least about 95 wt % p-DEB.

In adsorptive separation zone 100, adsorption conditions will include a temperature range from about 20° C. to about 300° C. In an embodiment the adsorption temperature will range from about 20° C. to about 250° C.; in another embodiment the range is from about 40° C. to about 200° C. The adsorption pressure is sufficient to maintain liquid phase, which may be from about 1 barg to about 40 barg. Desorption conditions may include the same range of temperatures and pressure as used for adsorption conditions. In a fixed bed embodiment, adsorptive separation zone 100 may use vapor phase desorption conditions to minimize the amount of desorbent that remains on the adsorbent when feed is next introduced.

Extract stream 5 removed from adsorptive separation zone 100 comprises the most strongly adsorbed feed components including para-xylene and, if present, para-methylethylbenzene (p-MEB) and toluene, which may be referred to extract compounds. Extract stream 5 also comprises desorbent compounds such as p-DEB and other components that may be present in desorbent stream 3 such as C9 aromatics. Although most of the C9 aromatics are raffinate compounds as described below, when such compounds are introduced to the adsorptive separation zone in the desorbent stream, they will pass through the adsorptive separation zone into the extract stream roughly in proportion to the composition of desorbent stream 3. For example the ratio of C9 aromatics, other than p-MEB, to p-DEB in desorbent stream 3 will be similar to the ratio of C9 aromatics, other than p-MEB, to p-DEB in extract stream 5. Extract stream 5 also includes trace amounts of one or more raffinate compounds that are introduced to the adsorptive separation zone via feed stream 1. Thus, extract stream 5 will comprise at least a trace amount of the C9 aromatic. In an embodiment, extract stream 5 comprises at least about 20 ppm by weight of C9 aromatics. In another embodiment extract stream 5 comprises at least about 100 ppm by weight of C9 aromatics; and extract stream 5 may comprise at least about 250 ppm by weight of C9 aromatics. Raffinate stream 7 removed from adsorptive separation zone 100 comprises desorbent compounds such as p-DEB, other desorbent components such as C9 aromatics, and the less strongly adsorbed feed components such as ethylbenzene, ortho-xylene, meta-xylene, and the C9 aromatics, other than p-MEB, which may be referred to raffinate compounds. Although a small amount of para-xylene and other extract compounds such as p-MEB may be present in raffinate stream 7, the raffinate stream C8 aromatics may be referred to as para-xylene depleted C8 aromatics.

In an embodiment, extract stream 5 withdrawn from adsorptive separation zone 100 is passed to extract distillation zone 200. Extract distillation zone 200 comprises extract distillation column 210 and extract distillation zone 200 produces para-xylene product stream 215 and a desorbent stream 220 which comprises p-DEB and the C9 aromatic. Distillation zone product streams are enriched, that is they have a higher concentration of a component or class of components relative to the concentration of the component or class of components in the stream being separated. Thus, para-xylene product stream 215 is enriched in para-xylene, i.e. the concentration of para-xylene is greater in para-xylene product stream 215 than in extract stream 5. Likewise, desorbent stream 220 is enriched in p-DEB as desorbent stream 220 has a higher concentration of p-DEB than the concentration of p-DEB in extract stream 5. In an embodiment, at least a portion of desorbent stream 220 removed from extract distillation zone 200 is recycled to adsorptive separation zone 100 for use as desorbent. This recycle step may be accomplished by using one or more flow paths. Exemplary flow paths from desorbent stream 220 include optional conduit 250 to desorbent stream 3, directly to adsorptive separation zone 100 via a conduit, not shown, and through one or more other conduits and/or zones as discussed below before reaching adsorptive separation zone 100. A portion or all of desorbent stream 220 may thus be recycled to adsorptive separation zone 100 in a single flow path or divided among multiple flow paths.

In other embodiments, the enrichment or purity of the distillation zone product streams may be increased. For example, para-xylene product stream 215 may comprise substantially all of the para-xylene in extract stream 5 from adsorption separation zone 100. As used herein, the term "substantially all" means an amount generally of at least 90%, preferably at least 95%, and optimally at least 99%, by weight, of a compound or class of compounds in a stream. In another embodiment, para-xylene product stream 215 comprises substantially all of the para-xylene in feed stream 1. For example, at least 90 wt % of the para-xylene in the feed stream may be recovered in para-xylene product stream 215. Desorbent stream 220 removed from extract distillation zone 200 may comprise substantially all of the p-DEB in extract stream 5. In an embodiment, para-xylene product stream 215 is the overhead or a light side-cut stream from extract distillation column 210 and desorbent stream 220 is the bottoms or a heavy side-cut stream from distillation column 210.

Those of ordinary skill in the art will understand that the process flow and connections of various zones described herein is sufficient to practice the invention. Unless otherwise stated, the exact connection point within the zones is not essential to the invention. For example, it is well known in the art that a stream to a distillation zone may be sent directly to the column, or the stream may first be sent to other equipment within the zone such as heat exchangers, to adjust temperature, and/or pumps to adjust the pressure. Likewise, streams leaving a zone may pass directly from a distillation column or they may first pass through an overhead or reboiler section before leaving the distillation zone.

Extract distillation zone 200 may also produce additional product streams. As illustrated in FIG. 1, a product stream lighter than para-xylene may be removed from extract distillation zone by optional conduit 230. For example, this embodiment may be used when light impurities in extract stream 5 such as toluene are removed to enable the para-xylene product 215 to meet desired purity specifications. Extract distillation zone 200 may be configured and operated as well known in the art to make three or more product streams, e.g. using a dividing wall distillation column, side draw streams, and/or additional distillation columns. In an embodiment, optional extract finishing distillation column 211 separates an overhead stream from extract distillation column 210 into the light impurity stream 230 and the para-xylene product stream 215.

Para-methylethylbenzene (p-MEB) in feed stream 1 and the C9 aromatics in desorbent stream 3 may also be present in extract stream 5 from adsorptive separation zone 100. Although it is often desired for para-xylene product 215 to contain at least 99.7 wt % para-xylene, it is not always necessary to strictly limit the amount of p-MEB in the para-xylene product 215. For example, where para-xylene product is oxidized to make terephthalic acid, oxidation of p-MEB results in the same product. Therefore, not removing p-MEB from para-xylene product 215 may actually be beneficial. However, unacceptable accumulation of p-MEB in extract distillation zone desorbent stream 220 may be managed in a number of ways. For example, the p-MEB content of feed stream 1 may be limited to a maximum amount. In an embodiment, the content of p-MEB in feed stream 1 to adsorptive separation zone 100 may be limited such that the amount of p-MEB in feed stream 1 is not more than about 0.05 wt % of the para-xylene in feed stream 1.

As recognized herein, desorbent stream 3 to adsorptive separation zone 100 may contain up to about 25 wt % C9 aromatic hydrocarbons including p-MEB. Thus, accumulation of p-MEB, if any, in the desorbent stream, may be managed in conjunction with managing the other C9 aromatics that may be present in extract stream 5. In an embodiment, desorbent stream 220 removed from extract distillation zone 200 further comprises substantially all of the C9 aromatics in extract stream 5. A portion or all of desorbent stream 220 may be passed via line 280 to another distillation zone such as desorbent distillation zone 400 to separate C9 aromatics from p-DEB.

In an embodiment not illustrated, extract distillation zone 200 produces a second extract distillation zone desorbent stream. As previously discussed, multiple product streams are readily accomplished by those of ordinary skill in the art of distillation. In this embodiment, desorbent stream 220 comprises p-DEB and C9 aromatic hydrocarbons and the second extract distillation zone desorbent stream has a higher boiling point than desorbent stream 220. Thus, in this embodiment, desorbent stream 220 is intermediate para-xylene product stream 215 and the second extract distillation zone desorbent stream, which comprises desorbent components. Although some portion of the C9 aromatic hydrocarbons in extract stream 5 may be found in each of the para-xylene product stream 215, intermediate desorbent stream 220, and the second extract distillation zone desorbent stream, the concentration of C9 aromatics (wt %) in the second extract distillation zone desorbent stream is less than the concentration of C9 aromatics (wt %) in desorbent stream 220. Concentrating the C9 aromatics in this manner provides greater flexibility in managing the C9 aromatic content of desorbent stream 3, and may facilitate C9 aromatic removal such as when at least a portion of the intermediate desorbent stream 220 is passed through conduits 220 and 280 to be separated in desorbent distillation zone 400. A portion of the second extract distillation zone desorbent stream may be recycled to adsorptive separation zone 100.

As illustrated in FIG. 1, raffinate stream 7 from adsorptive separation zone 100 is passed to raffinate distillation zone 300. Raffinate distillation zone 300 comprises raffinate distillation column 310 and raffinate distillation zone 300 produces raffinate product stream 315 and desorbent stream 320. In an embodiment, raffinate product stream is enriched in C8 aromatics relative to raffinate stream 7 and desorbent stream 320 is enriched in p-DEB relative to raffinate stream 7. In another embodiment, desorbent stream 320 is enriched in C9 aromatics relative to raffinate stream 7. Optionally, raffinate product stream 315 may comprise no more than about 1 wt % para-xylene. In another embodiment, raffinate product stream 315 comprises substantially all of the C8 aromatics (the para-xylene depleted C8 aromatic hydrocarbons) in raffinate stream 7. Raffinate product stream 315 may be the overhead or a light side-cut stream from raffinate distillation column 310 and the bottoms or a heavy side-cut stream from distillation column 310 may be desorbent stream 320. Desorbent stream 320 removed from raffinate distillation zone 300 comprises C9 aromatics and p-DEB. Desorbent stream 320 may comprise substantially all of the C9 aromatics in raffinate stream 7. In another embodiment, desorbent stream 320 removed from raffinate distillation zone 300 comprises substantially all of the C9 aromatics and p-DEB in raffinate stream 7. In an embodiment, at least a portion of desorbent stream 320 removed from raffinate distillation zone 300 is recycled to adsorptive separation zone 100 for use as desorbent. This recycle step may be accomplished by using one or more flow paths. Exemplary flow paths from desorbent stream 320 include optional conduit 350 to desorbent stream 3, directly to adsorptive separation zone 100 via a conduit, not shown, and through one or more other conduits and/or zones as discussed below before reaching adsorptive separation zone 100. A portion or all of desorbent stream 320 may thus be recycled to adsorptive separation zone 100 in a single flow path or divided among multiple flow paths.

In an embodiment not illustrated, raffinate distillation zone 300 produces a second raffinate distillation zone desorbent stream. As previously discussed, multiple product streams are readily accomplished by those of ordinary skill in the art of distillation. Raffinate product stream 315 comprises para-xylene depleted C8 aromatic hydrocarbons, desorbent stream 320 comprises p-DEB and C9 aromatic hydrocarbons and the second raffinate distillation zone desorbent stream has a higher boiling point than desorbent stream 320. Thus, in this embodiment, desorbent stream 320 is intermediate raffinate product stream 315 and the second raffinate distillation zone desorbent stream, which comprises desorbent components. Although some portion of the C9 aromatic hydrocarbons in raffinate stream 7 may be found in each of raffinate product stream 315, intermediate desorbent stream 320, and the second raffinate distillation zone desorbent stream, the concentration of C9 aromatics (wt %) in the second raffinate distillation zone desorbent stream is less than the concentration of C9 aromatics (wt %) in desorbent stream 320. Concentrating the C9 aromatics in this manner provides greater flexibility in managing the C9 aromatic content of desorbent stream 3, and may facilitate C9 aromatic removal such as when at least a portion of the intermediate desorbent stream 320 is passed through conduits 320 and 380 to be separated in desorbent distillation zone 400. A portion of the second raffinate distillation zone desorbent stream may be recycled to adsorptive separation zone 100.

At least a portion of a stream comprising p-DEB and C9 aromatics is passed to desorbent distillation zone 400 as a desorbent distillation zone feed stream. Examples of such streams include desorbent streams 220, 280, 320, and 380, the second extract distillation zone desorbent stream, and the second raffinate distillation zone desorbent stream. Desorbent distillation zone 400 comprises desorbent distillation column 410 and desorbent distillation zone 400 produces C9 aromatic product stream 415 and desorbent stream 420. In an embodiment, C9 aromatic product stream 415 is enriched in C9 aromatics relative to the desorbent distillation zone feed stream and desorbent stream 420 is enriched in p-DEB relative to the desorbent distillation zone feed stream. C9 aromatic product stream 415 may be the overhead or a light side-cut stream from desorbent distillation column 410 and desorbent stream 420 may be the bottoms or a heavy side-cut stream from distillation column 410. In an embodiment, desorbent stream 420 comprises substantially all of the p-DEB in the desorbent distillation zone feed stream. At least a portion of desorbent stream 420 is recycled, e.g. via line 450, to adsorptive separation zone 100 for use as desorbent. Desorbent distillation zone 400 thus prevents unacceptable accumulation of C9 aromatic hydrocarbons in desorbent stream 3 which is introduced to adsorptive separation zone 100 by separating C9 aromatics from p-DEB and removing or recovering the C9 aromatics in C9 aromatic product stream 415.

The C9 aromatic hydrocarbon content and other specifications of desorbent stream 3 that is introduced into adsorptive separation zone 100 may be controlled, for example, by regulating C9 aromatic composition in the feed stream, the operating conditions in the extract distillation zone 200, raffinate distillation zone 300, and desorbent distillation zone 400, and the portions of the streams comprising desorbent that are recycled from each of the distillation zones to contribute to desorbent stream 3. The invention thus provides a variety of options for the efficient management of C9 aromatic hydrocarbons within the process. For example, the C9 aromatic/p-DEB separation in desorbent distillation zone 400 may be facilitated by limiting the amount of the highest boiling C9 aromatic, 123 trimethylbenzene, in the feed stream to the adsorptive separation zone. In an embodiment, the feed stream comprises no more than about 0.1 wt % 123 trimethylbenzene. In another embodiment, the feed stream comprises no more than about 0.05 wt % 123 trimethylbenzene. In an embodiment, the feed stream C9 aromatic is selected from the group consisting of 135-trimethylbenzene, 123-trimethylbenzene, 124-trimethylbenzene, n-propylbenzene, isopropylbenzene, meta-methylethylbenzene, ortho-methylethylbenzene, and combinations thereof. In another embodiment, the feed stream C9 aromatic is selected from the group consisting of n-propylbenzene, isopropylbenzene, meta-methylethylbenzene, ortho-methylethylbenzene, 135-trimethylbenzene, 124-trimethylbenzene, and combinations thereof.

Although higher concentrations of C9 aromatics in the desorbent stream is known to be detrimental, for example, by increasing utility costs and occupying volume in the process, the invention recognizes that higher levels of C9 aromatics in the desorbent may also provide benefits, such as, minimizing p-DEB losses when C9 aromatics are distilled from the desorbent and enabling higher levels of C9 aromatics in the feed stream. Higher concentrations of C9 aromatics in the desorbent stream may result from higher levels of C9 aromatics in the feed stream and/or permitting increased accumulation of C9 aromatics in the desorbent stream.

The instant invention recognizes that desorbent introduced to adsorptive separation zone 100 may comprise as much as 25 wt % C9 aromatics. In an embodiment, the C9 aromatic content of desorbent stream 3 ranges from about 0.5 wt % to about 15 wt %. In another embodiment, the C9 aromatic content of desorbent stream 3 ranges from about 1 wt % to about 5 wt %.; in another embodiment, the range is from about 3 wt % to about 15 wt % C9 aromatics. In an embodiment, C9 aromatic product stream 415 comprises at least about 2.5% of the C9 aromatics in the desorbent distillation zone feed stream. In another embodiment, C9 aromatic product stream 415 comprises at least about 10% of the C9 aromatics in the desorbent distillation zone feed stream; C9 aromatic product stream 415 may comprise substantially all of the C9 aromatics in the desorbent distillation zone feed stream.

Figure 2:
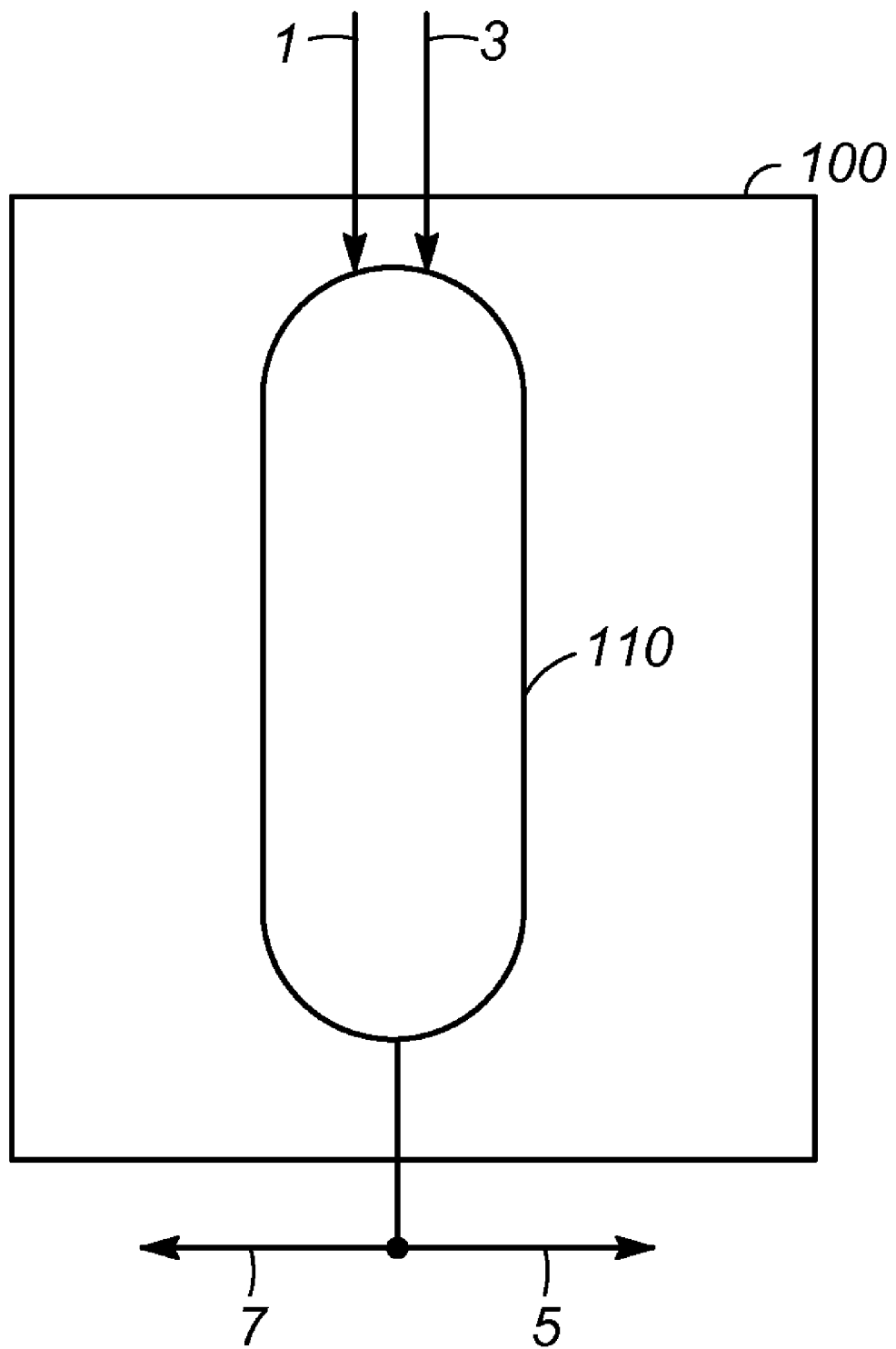
FIG. 2 is a simplified flow scheme of an adsorptive separation zone of the invention illustrating a fixed bed embodiment.

The invention is not limited by the type or mode of adsorptive separation. In a batch mode embodiment, an adsorptive separation zone comprises an adsorbent chamber having one or more vessels containing adsorbent in one or more beds. Batch mode operation consists of sequentially introducing feed then desorbent into the adsorbent chamber. The adsorbent is thus subjected to alternate adsorption and desorption steps that produce a raffinate stream and an extract stream which alternately flow out of the adsorbent chamber. In an embodiment, adsorptive separation zone 100 may operate in a batch mode as illustrated in FIG. 2. Feed stream is introduced via conduit 1 and the desorbent stream is introduced via conduit 3. Thus, conduits 1 and 3 are alternately active in providing fluid communication to adsorptive separation zone 100. Likewise, the raffinate 7 and extract 5 conduits are alternately active in providing fluid communication of the raffinate and extract streams, respectively, from adsorptive separation zone 100. As shown, the streams may enter or exit the adsorbent chamber through individual inlets or a common inlet with valves, not shown, controlling the flows as is commonly known.

In swing bed mode, the adsorbent chamber comprises at least two adsorbent beds or vessels each of which is operated in batch mode wherein the adsorbent beds may be operating at different steps of the adsorption/desorption cycle. Swing bed mode may approach continuous production when the adsorbent chamber includes sufficient vessels operating at different points in time of the adsorption/desorption cycle to provide more uniform product quality from the overall adsorptive separation zone. Both the batch mode and swing bed modes are types of fixed bed adsorptive separation processes. In fixed bed adsorptive separations, desorption conditions may be similar to the adsorption conditions. In another embodiment, vapor phase desorption conditions may be used to minimize the amount of desorbent remaining on the adsorbent when feed is introduced to begin the next adsorption/desorption cycle. For example, the desorption pressure may be decreased and/or the temperature may be increased relative to the adsorption conditions.

In an embodiment, adsorptive separation zone 100 is a fixed bed adsorptive separation zone. The adsorptive separation zone may operate as a moving bed adsorptive separation system wherein adsorbent moves through the adsorbent chamber while the feed and desorbent streams are introduced to and the extract and raffinate streams are withdrawn from the adsorbent chamber at separate fixed locations. In another embodiment, the adsorptive separation zone 100 is a simulated moving bed (SMB) adsorptive separation zone.

Figure 3:
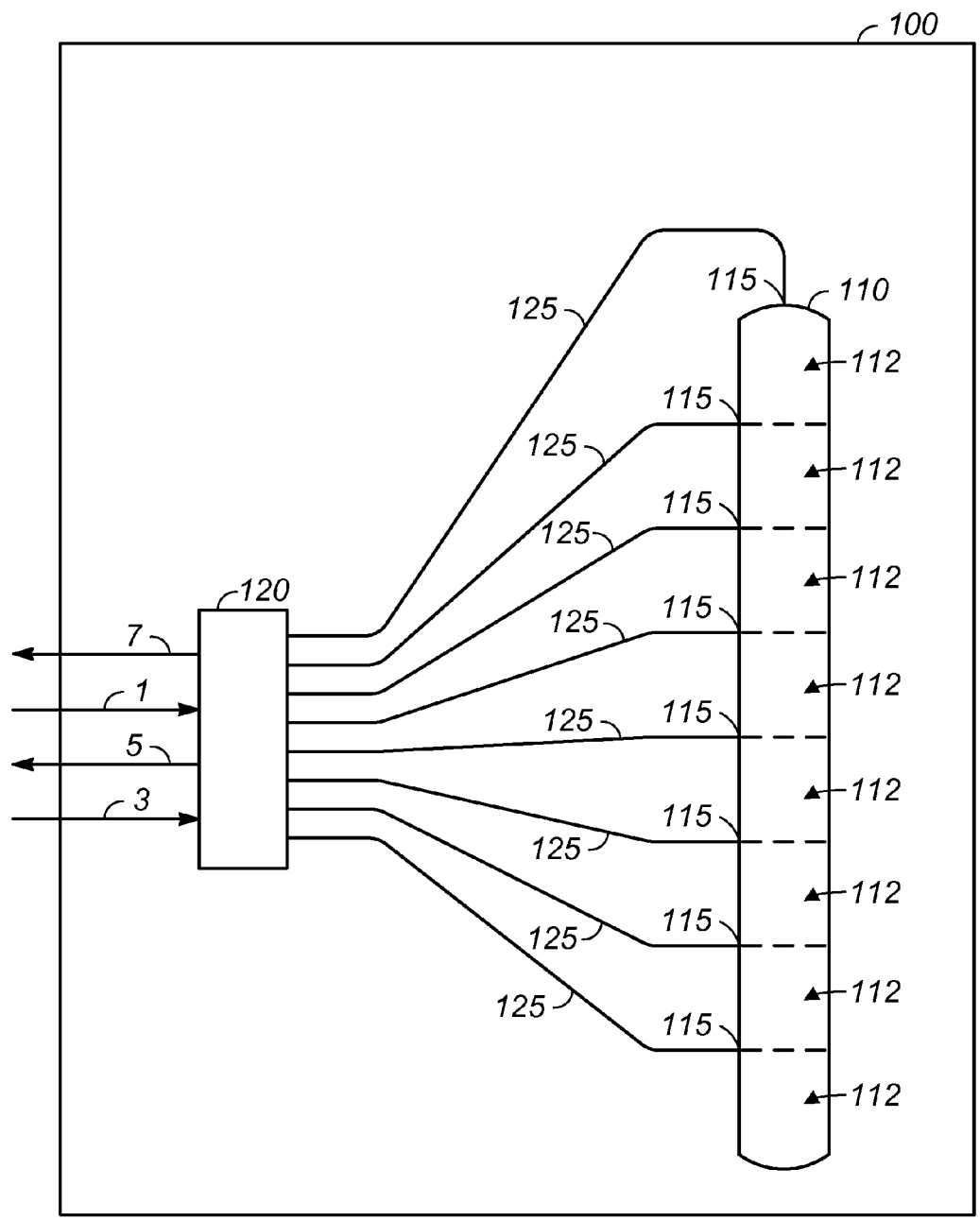
FIG. 3 is a simplified flow scheme of an adsorptive separation zone of the invention illustrating a simulated moving bed embodiment.

FIG. 3, illustrates an embodiment wherein adsorptive separation zone 100 operates as a simulated moving bed (SMB) comprising an adsorbent chamber 110 having at least eight transfer points 115, a fluid distributor 120, and at least one transfer line 125 providing fluid communication between each transfer point and the fluid distributor. The adsorbent chamber 110 contains a number of separate beds 112 of an adsorbent selective for para-xylene. Each bed is in fluid communication with one of the transfer points. In an embodiment the adsorbent chamber has 16 transfer points. In another embodiment the adsorbent chamber comprises two vessels connected in series, each vessel having 12 transfer points.

In the SMB embodiment, four primary process streams: the feed, desorbent, extract, and raffinate streams are passed simultaneously into and out of the adsorptive separation zone as the adsorption and desorption steps are carried out simultaneously. Feed conduit 1 and desorbent conduit 3 provide fluid communication to fluid distributor 120. The raffinate conduit 7 and extract conduit 5 provide fluid communication from fluid distributor 120. The fluid distributor directs the process streams to and from the adsorbent chamber 110 via transfer lines 125 and transfer points 115. At least four of the transfer line/transfer point pairs are active at a given time. That is, each of the four primary process streams flows through one transfer line/point pair. Additional transfer line/point pairs may also be active when optional streams flow to or from the adsorbent chamber. Examples of optional streams are given in U.S. Pat. No. 3,201,491 and U.S. Pat. No. 4,319,929.

The fluid distributor 120 and an associated controller, not shown, increment the location of the active transfer lines/points periodically along the adsorbent chamber to the next transfer point to simulate movement of the adsorbent in the opposite direction of the transfer point movement. In an embodiment, the locations of the active transfer points are shifted down the adsorbent chamber to simulate upward movement of the adsorbent, and the fluid phase is circulated through the adsorbent chamber in a downward direction. Although not shown in the drawing, the first and last beds in the adsorbent chamber are connected via a conduit and pump to ensure continuous fluid flow in the desired direction. The operating steps, principles, and equipment used in SMB adsorptive separations are well known in the art. U.S. Pat. No. 2,985,589; U.S. Pat. No. 3,310,486; and U.S. Pat. No. 3,686,342 are herein incorporated by reference for their teachings with respect to SMB adsorptive separations.

In SMB adsorptive separation processes, the steps or operational zones in the adsorbent chamber are defined by the position of the input and output streams as follows. Zone 1, the adsorption zone, includes the adsorbent between the feed inlet and raffinate outlet. Zone 2, the purification zone, includes the adsorbent between the feed inlet and the extract outlet and is located upstream of Zone 1. Zone 3, the desorption zone, includes the adsorbent between the extract outlet and the desorbent inlet and is located upstream of Zone 2. Optional Zone 4, a buffer zone, where used includes the adsorbent between the desorbent inlet and the raffinate outlet. Further details on equipment and techniques in an SMB process may be found, for example, in U.S. Pat. No. 3,208,833; U.S. Pat. No. 3,214,247; U.S. Pat. No. 3,392,113; U.S. Pat. No. 3,455,815; U.S. Pat. No. 3,523,762; U.S. Pat. No. 3,617,504; U.S. Pat. No. 4,133,842; and U.S. Pat. No. 4,434,051.

The fluid distributor 120 may be a rotary valve type as described in U.S. Pat. No. 3,040,777; U.S. Pat. No. 3,422,848; and U.S. Pat. No. 4,409,033 or a manifold/multivalve type system as in U.S. Pat. No. 4,434,051. Co-current SMB operations as described in U.S. Pat. No. 4,402,832 and U.S. Pat. No. 4,498,991 may also be used. Equipment utilizing these principles is familiar, in sizes ranging from pilot plant scale as in U.S. Pat. No. 3,706,812 to commercial scale having flow rates from a few cc per hour to many thousands of gallons per hour. The invention may also be practiced in a co-current, pulsed batch process, like that described in U.S. Pat. No. 4,159,284 or in a co-current, pulsed continuous process, like that disclosed in U.S. Pat. Nos. 4,402,832 and 4,478,721.

The invention claimed is:

1. A process for separating para-xylene from a feed stream comprising para-xylene, at least one other C8 aromatic, and a C9 aromatic, the process comprising:
   (a) contacting an adsorbent comprising a zeolite with the feed stream and a first desorbent stream in an adsorptive separation zone to produce an extract stream and a raffinate stream, the zeolite selected from the group of zeolites consisting of Y zeolites and X zeolites, the first desorbent stream comprising para-diethylbenzene, the extract stream comprising para-xylene, para-diethylbenzene, and the C9 aromatic, and the raffinate stream comprising para-diethylbenzene, the at least one other C8 aromatic, and the C9 aromatic;
   (b) passing the extract stream to an extract distillation zone to produce a para-xylene product stream, and a second desorbent stream comprising para-diethylbenzene and the C9 aromatic;
   (c) passing the raffinate stream to a raffinate distillation zone to produce a raffinate product stream comprising the at least one other C8 aromatic, and a third desorbent stream comprising para-diethylbenzene and the C9 aromatic;
   (d) passing at least a portion of at least one of the second desorbent stream and the third desorbent stream to a desorbent distillation zone to produce a fourth desorbent stream comprising para-diethylbenzene, and a C9 aromatic product stream comprising the C9 aromatic; and
   (e) recycling at least a portion of the fourth desorbent stream to step (a) as at least a portion of the first desorbent stream.

2. The process of claim 1 wherein the C9 aromatic is selected from the group consisting of n-propylbenzene, iso-propylbenzene, meta-methylethylbenzene, ortho-methylethylbenzene, 135-trimethylbenzene, 123-trimethylbenzene, 124-trimethylbenzene, and combinations thereof.

3. The process of claim 1 wherein the C9 aromatic is selected from the group consisting of n-propylbenzene, iso-propylbenzene, meta-methylethylbenzene, ortho-methylethylbenzene, 135-trimethylbenzene, 124-trimethylbenzene, and combinations thereof.

4. The process of claim 1 wherein the feed stream comprises no more than about 25 wt % C9 aromatics.

5. The process of claim 1 wherein the feed stream comprises C9 aromatics in an amount ranging from about 0.1 wt % to about 15 wt % of the feed stream.

6. The process of claim 1 wherein the feed stream comprises C9 aromatics in an amount ranging from about 0.3 wt % to about 5 wt % of the feed stream.

7. The process of claim 1 wherein the first desorbent stream comprises no more than about 25 wt % C9 aromatics.

8. The process of claim 1 wherein the feed stream comprises no more than about 10 ppm-mass of C10+ aromatic hydrocarbons.

9. The process of claim 1 wherein the first desorbent stream comprises C9 aromatics in an amount ranging from about 0.5 wt % to about 15 wt % of the first desorbent stream.

10. The process of claim 1 wherein the feed stream comprises para-methylethylbenzene in an amount not more than about 0.05 wt % of the para-xylene in the feed stream.

11. The process of claim 1 further comprising recycling at least a portion of the second desorbent stream to step (a) as at least a portion of the first desorbent stream.

12. The process of claim 1 further comprising recycling at least a portion of the third desorbent stream to step (a) as at least a portion of the first desorbent stream.

13. The process of claim 1 wherein the raffinate distillation zone further produces a fifth desorbent stream, the fifth desorbent stream having a lower wt % concentration of C9 aromatics than the wt % concentration of C9 aromatic hydrocarbons of the third desorbent stream and recycling at least a portion of the fifth desorbent stream to step (a) as at least a portion of the first desorbent stream.

14. The process of claim 1 wherein the extract distillation zone further produces a sixth desorbent stream, the sixth desorbent stream having a lower wt % concentration of C9 aromatics than the wt % concentration of C9 aromatic hydrocarbons of the second desorbent stream and recycling at least a portion of the sixth desorbent stream to step (a) as at least a portion of the first desorbent stream.

15. The process of claim 1 wherein the C9 aromatic product stream comprises at least about 2.5% of the C9 aromatics in the at least a portion of at least one of the second desorbent stream and the third desorbent stream passing to the desorbent distillation zone.

16. The process of claim 1 wherein the C9 aromatic product stream comprises between about 2.5% and about 10% of the C9 aromatics in the at least a portion of at least one of the second desorbent stream and the third desorbent stream passing to the desorbent distillation zone.

17. The process of claim 1 wherein the zeolite further comprises barium.

18. The process of claim 1 wherein the adsorptive separation zone is a simulated moving bed adsorptive separation zone.

19. The process of claim 18 wherein the simulated moving bed adsorptive separation zone operates in counter-current mode at a temperature ranging from about 20° C. to about 300° C. and a pressure ranging from about 1 barg to about 40 barg.

20. The process of claim 1 wherein, the feed stream comprises no more than about 0.1 wt % of 123 trimethylbenzene.

* * * * *